United States Patent
Lowe et al.

(10) Patent No.: US 9,649,037 B2
(45) Date of Patent: May 16, 2017

(54) METHOD AND APPARATUS FOR HEMODYNAMIC MONITORING USING COMBINED BLOOD FLOW AND BLOOD PRESSURE MEASUREMENT

(75) Inventors: Graham Desmond Lowe, Hayling Island (GB); Richard John Willshire, Chichester (GB); Leonard Smith, Ringwood (GB); Andrew Jones, Haywards Heath (GB); Ewan Alistair Phillips, Richmond (GB)

(73) Assignee: DELTEX MEDICAL LIMITED, Chichester, West Sussex (GB)

( * ) Notice: Subject to any disclaimer, the term of this patent is extended or adjusted under 35 U.S.C. 154(b) by 578 days.

(21) Appl. No.: 12/958,614

(22) Filed: Dec. 2, 2010

(65) Prior Publication Data
US 2011/0137173 A1 Jun. 9, 2011

Related U.S. Application Data

(60) Provisional application No. 61/266,266, filed on Dec. 3, 2009.

(51) Int. Cl.
*A61B 8/00* (2006.01)
*A61B 5/0215* (2006.01)
(Continued)

(52) U.S. Cl.
CPC ............ *A61B 5/02152* (2013.01); *A61B 8/04* (2013.01); *A61B 8/06* (2013.01); *A61B 8/08* (2013.01);
(Continued)

(58) Field of Classification Search
CPC ......... A61B 8/08; A61B 5/0048; A61B 5/031; A61B 5/4519; A61B 5/4824; A61B 5/4869; A61B 6/503; A61B 6/504; A61B 8/00; A61B 8/04; A61B 8/065; A61B 8/0808; A61B 8/0816; A61B 8/0883;
(Continued)

(56) References Cited

U.S. PATENT DOCUMENTS 4,257,278 A * 3/1981 Papadofrangakis et al. .......................... 73/861.25
4,858,614 A 8/1989 Stevens et al.
(Continued)

*Primary Examiner* — Amanda Lauritzen Moher
(74) *Attorney, Agent, or Firm* — Day Pitney LLP

(57) ABSTRACT

Combined blood flow and blood pressure measurements are used for the calculation of central vascular blood flow parameters. Blood flow measurements may be made simultaneously with arterial pressure measured either centrally or peripherally and central venous pressure for the monitoring of human subjects. A combined blood flow and blood pressure measurement device for hemodynamic monitoring may include a Doppler ultrasound probe utilizing a continuous wave or pulse wave ultrasound beam for the measurement of blood flow in the aorta, combined with arterial pressure measurement, or signal input from a suitable pressure transducer system from one of either the radial, brachial, dorsalis pedis or femoral artery. The ultrasound probe may comprise either an esophageal or suprasternal ultrasound probe, while the blood pressure measurement may be either an electronic transducer blood pressure sphygmomanometer on the arm, or a finger cot infrared light optical pulse detector.

26 Claims, 3 Drawing Sheets

(51) Int. Cl.
*A61B 8/06* (2006.01)
*A61B 8/08* (2006.01)
*A61B 8/12* (2006.01)
*A61B 8/04* (2006.01)

(52) U.S. Cl.
CPC .............. *A61B 8/0891* (2013.01); *A61B 8/12* (2013.01); *A61B 8/445* (2013.01); *A61B 8/4483* (2013.01); *A61B 8/488* (2013.01)

(58) Field of Classification Search
CPC ..... A61B 8/0891; A61B 5/02152; A61B 8/06; A61B 8/12; A61B 8/445; A61B 8/4483; A61B 8/488
See application file for complete search history.

(56) References Cited

U.S. PATENT DOCUMENTS

| | | | | |
|---|---|---|---|---|
| 5,038,789 | A * | 8/1991 | Frazin | A61B 8/06 600/471 |
| 5,450,850 | A | 9/1995 | Iinuma | |
| 5,479,928 | A | 1/1996 | Cathignol | |
| 5,503,156 | A | 4/1996 | Millar | |
| 5,844,140 | A * | 12/1998 | Seale | 73/633 |
| 2004/0059220 | A1 * | 3/2004 | Mourad et al. | 600/442 |
| 2006/0167363 | A1 | 7/2006 | Osypka et al. | |
| 2007/0093702 | A1 * | 4/2007 | Yu | A61B 5/14551 600/326 |
| 2007/0191724 | A1 | 8/2007 | Hirsh | |
| 2008/0039722 | A1 * | 2/2008 | Mejia | A61B 5/0006 600/437 |
| 2010/0036253 | A1 * | 2/2010 | Vezina | A61B 5/02028 600/453 |

\* cited by examiner

METHOD AND APPARATUS FOR HEMODYNAMIC MONITORING USING COMBINED BLOOD FLOW AND BLOOD PRESSURE MEASUREMENT

CROSS REFERENCE TO RELATED APPLICATION

This application claims the benefit of U.S. Provisional Application No. 61/266,266, filed Dec. 3, 2009.

FIELD OF THE INVENTION

The present invention relates to a method and apparatus for the measurement of central vascular blood flow simultaneously with arterial blood pressure measured either centrally or peripherally for the monitoring of human subjects.

BACKGROUND

Historically medical practice for the measurement of hemodynamic blood flow parameters has been based on the use of a pulmonary artery catheter. This device is highly invasive and requires a catheter to be introduced through a large vein—often the internal jugular, subclavian, or femoral vein. The catheter is threaded through the right atrium and ventricle of the heart and into the pulmonary artery. The standard pulmonary artery catheter (Swan-Ganz) has two lumens (tubes) and is equipped with an inflatable balloon at the tip, which facilitates its placement into the pulmonary artery through the flow of blood. The balloon, when inflated, causes the catheter to "wedge" in a small pulmonary blood vessel. So wedged, the catheter can provide a measurement of the blood pressure in the left atrium of the heart, termed Left Ventricular End Diastolic Pressure or LVEDP. Modern catheters have multiple lumens (multiple tubes) five or six are common and have openings along the length to allow administration of inotropes and other drugs directly into the right atrium of the heart. The addition of a small thermistor temperature probe about 3 centimeters behind the tip allows the measurement of blood flow following calibration by means of the injection of a known volume and known temperature of cold fluid. As this cooler fluid passes the thermistor, a brief drop in the blood temperature is recorded. The resulting information can be used to compute and plot a thermodilution curve. If details about the patient's body mass index, core temperature, systolic, diastolic, central venous pressure and pulmonary artery pressure are input, a comprehensive blood flow and pressure map can be calculated. The procedure is not without risk, and complications can be life threatening. It can lead to arrhythmias, rupture of the pulmonary artery, thrombosis, infection, pneumothorax, bleeding etc. The benefit of the use of this type of catheter device has been controversial and as a result many clinicians have limited its use.

Current hemodynamic monitoring systems rely on one of a variety of technologies namely; ultrasound Doppler flow measurement; arterial pressure utilizing mathematical algorithms to derive blood flow; electrical signals from skin electrodes; rebreathing pulmonary gas exchange; and mechanical accelerometry.

The measurement of vascular blood flow by use of ultrasound and the Doppler principle is widely used. A probe containing piezo-electric crystals driven to emit either continuous wave or pulse wave ultrasound is located close to an arterial blood vessel. The probe may be located either in the esophagus, trachea or is placed on the body surface in a position where an artery can be accessed such as at the suprasternal notch. The velocity of the blood flow is calculated using the Doppler equation:

$$v = \frac{c \cdot f_D}{2 \cdot f_T \cos\theta}$$

where v is the velocity of the red blood cells, c is the speed of the ultrasound waves through body tissues, $f_D$ is the Doppler frequency shift, $f_T$ is the transmitted frequency of the ultrasound and $\cos\theta$ is the cosine of the angle of insonation between the sound beam axis and the direction of blood flow. Flow based measurements using ultrasound are well suited to use in hemodynamically unstable patients where rapid and frequent changes in blood flow and pressure are encountered. An ultrasound beam directed into the vascular system provides accurate real time measurement of blood flow. However, the ultrasound beam is directional and is sensitive to movement, which requires the operator to check the beam's focus and thus the device cannot be considered to be providing continuous monitoring without operator attendance.

A second approach utilizes pressure measurements of arterial blood pressure measured invasively through an arterial cannula placed in an artery usually radial, femoral, dorsalis pedis or brachial. The cannula must be connected to a sterile, fluid-filled system, which is connected to an electronic pressure transducer. The advantage of this system is that pressure is constantly monitored beat-by-beat, and a waveform (a graph of pressure against time) can be displayed. Cannulation for invasive vascular pressure monitoring may be associated with complications such as extravasation, thrombosis and infection. Patients with invasive arterial monitoring require very close supervision, as there is a danger of severe bleeding if the line becomes disconnected. There are a variety of invasive vascular pressure monitors these include single pressure, dual pressure, and multi-parameter (i.e. pressure/temperature). Vascular pressure parameters such as systolic, diastolic and mean arterial pressure are derived and displayed simultaneously for pulsatile waveforms. Such devices utilize pulse contour or pulse pressure wave analysis where the area under the systolic pressure wave curve is integrated or wave characteristics are analyzed, and when calibrated against either dye dilution or thermodilution, provide estimates of blood flow volume. These systems are known to have good correlation to blood flow based measurements in hemodynamically stable patients as assessed by comparison to measurements made by a pulmonary artery catheter. However, these devices are known to be problematic in monitoring rapid changes in patients who are hemodynamically unstable. These devices can lead to erroneous cardiac output measurements during the administration of vaso-active drugs, during loss of circulating volume e.g. hemorrhage, insufflation of the abdomen for laparoscopic surgery, pathophysiological diseases resulting in abnormal arterial pressure waves and positional changes during surgery. Drugs which create vasoconstriction result in an increase in systemic resistance and thus increase in pressure which is interpreted as an increase in flow. Whereas blood flow typically decreases as systemic resistance increases as the heart is acting to pump against increased resistance. Conversely drugs which have a vasodilation effect result in a decrease in resistance to blood flow and typically blood pressure falls which is interpreted as a reduction in flow. Whereas blood flow typically increases as systemic resistance decreases as the heart is acting to pump against a reduced resistance. Calibration is essential for absolute value accuracy and in operating room conditions such calibration is complex to perform, is time consuming, needs to be repeated frequently, introduces chemical agents which may be toxic and may be of limited accuracy in the presence of other drugs administered during patient treatment.

Thus, there is a need in the art for an improved method and apparatus for hemodynamic monitoring using combined flow and pressure measurement information, which overcomes one or more of the aforementioned drawbacks.

BRIEF SUMMARY OF THE INVENTION

Figure 1A:
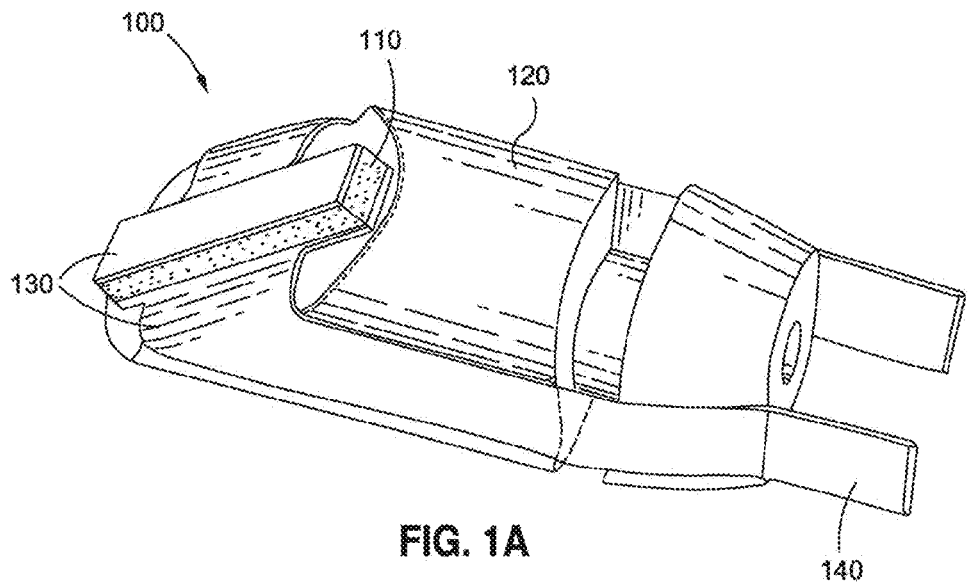
FIGS. 1A-1B depict one or more embodiments of an esophageal probe; with the high aspect ratio pulse wave ultrasound piezo-electric crystal assembly configured in accordance with the principles of the invention; alternatively with a crystal configuration designed for use with continuous wave ultrasound.

Disclosed and claimed herein are methods and devices for providing combinations of blood flow and blood pressure measurements for the calculation of central vascular blood flow parameters. Blood flow measurements may be made simultaneously with arterial pressure measured either centrally or peripherally and central venous pressure for the monitoring of human subjects. In one embodiment, a combined blood flow and blood pressure measurement device for hemodynamic monitoring may include a Doppler ultrasound probe utilizing a continuous wave or pulse wave ultrasound beam for the measurement of blood flow in the descending aorta, combined with arterial pressure measurement, or signal input from a suitable pressure transducer system from one of either the radial, brachial, dorsalis pedis or femoral artery. The above Doppler ultrasound probe may comprise either an esophageal or suprasternal Doppler ultrasound probe, while the blood pressure measurement may be provided by either an electronic transducer blood pressure sphygmomanometer on the arm, or alternatively by a finger cot infrared light optical pulse detector.

Additionally, the suprasternal Doppler ultrasound monitor may also utilize a continuous wave or pulse wave ultrasound beam for the measurement of blood flow in the ascending or descending aorta, combined with arterial pressure measurement or signal input from a suitable pressure transducer system from one of either the radial, brachial, dorsalis pedis or femoral artery, combined with arterial pressure measurement from one of either an electronic transducer blood pressure sphygmomanometer on the arm, or finger cot infrared light optical pulse detector. The system or device may further be configured to also provide central venous pressure measurement and/or mixed venous oxygen saturation.

Other aspects, features, and techniques of the invention will be apparent to one skilled in the relevant art in view of the following detailed description of the invention.

DETAILED DESCRIPTION OF EXEMPLARY EMBODIMENTS

One aspect of the invention is to combine the beneficial attributes of flow, as measured by Doppler ultrasound, with pressure as measured by way of standard arterial line technologies. Another aspect of the invention is to integrate the low invasive nature of Doppler ultrasound, its accuracy, responsiveness and ease of use in the hemodynamically unstable patient as typically encountered during surgery, with the continuous measurement capability of pressure based systems using an arterial line. Other measurements monitored clinically such as central venous pressure and mixed venous oxygen saturation could also be combined providing the basis for additional calculations such as delivered oxygen and oxygen consumption. Furthermore, the ability to measure flow and pressure simultaneously may provide additional parameters to clinicians for use in patient treatment. The improved monitor may provide accurate measurements of stroke distance, minute distance, stroke volume, stroke volume index, heart rate, cardiac output, cardiac index, peak velocity, mean acceleration, flow time corrected, flow time to peak, central venous pressure, systemic vascular resistance, systemic vascular resistance index, pulse pressure, aortic inertia, elastance, impedance, time to peak pressure, left ventricular force, left ventricular work, left ventricular power and total systemic vascular resistance. Certain embodiments of the invention may also provide the capability afforded by the combination of flow and pressure measurement in a wide range of applications and where applicable be minimally invasive (esophageal access) or non-invasive (suprasternal Doppler or external pressure sensor) in nature.

Still another aspect of the invention is to provide enhanced focusing capability of the Doppler ultrasound flow monitor by way of a wider beam angle and use of pulse wave Doppler ultrasound to restrict the depth of view and minimize confounding signals. In certain embodiments, the device may provide the user with a variety of modes of measurement to suit the application. It is envisaged that the monitor may allow the connection of alternate probes and sensors for flow and pressure measurement. Additionally monitor lines measuring oxygen concentration may also be connected to the monitor. Flow based Doppler ultrasound measurements may be available either by way of esophageal placement of the ultrasound for minimally invasive measurement in the descending aorta or by way of non-invasive suprasternal placement for measurement in the ascending aorta. Pressure measurements or signals may be obtained either invasively from an arterial line placed in either the radial, femoral, dorsalis pedis or brachial artery or by way of blood pressure in the brachial artery using an upper arm cuff or by way an infrared light optical sensor measuring pulse pressure in the patient's fingertip; or a central venous pressure signal obtained from a suitable pressure transducer system.

Data from both the flow and pressure measurement sensors may be analyzed to provide real time displays of the left ventricular flow waveform. In certain embodiments, the Doppler measurement may be utilized to frequently calibrate the pressure wave so providing continuous and accurate vascular flow information during any temporary loss of Doppler ultrasound sensor measurement due to loss of beam focus or electromagnetic interference. The data may also be processed to provide an extensive range of hemodynamic parameters for clinical use. Data from both the flow and pressure measurement sensors may be analyzed to provide trended parameters averaged over time. This trend data may be presented continuously either graphically or as bar charts.

With respect to the various data processing functionality described herein, it should be appreciated that an ultrasound probe configured in accordance with the principles of the invention may be configured with an internal microcomputer configured to carrying out such data processing operations, including but not limited to analyzing patient-specific physiological information, or otherwise processing blood flow measurement information and blood pressure information. Alternatively, the ultrasound probe may be connected to an external host processor that performs such data processing.

Referring now to the figures, FIG. 1A depicts one embodiment of a device configured in accordance with the principles of the invention. The device of FIG. 1A depicts a piezo-electric crystal esophageal Doppler probe head assembly 100 driven by pulse wave ultrasound. The piezo-electric crystal 110 may be affixed to a solid carrier material 120, as shown. Additionally, the piezo-electric crystal 110 may be electrically connected by way of flexible printed circuit boards 130 which may have the advantage of connection to the piezo-electric crystal 110 by way of conductive adhesives avoiding difficult micro soldering processes to the heat sensitive piezo-electric material. In certain embodiments, the flexible printed circuit boards 130 may include cable connection terminals 140 for ease of solder connection to a cable behind/below the solid crystal carrier 120. Alternatively the piezo-electric crystal 110 may be connected to the cable directly.

Figure 1B:
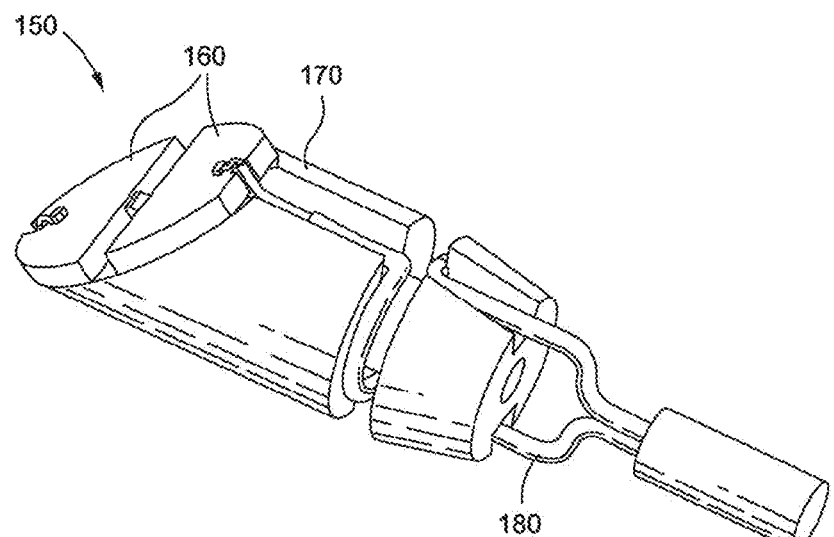

FIG. 1B depicts a piezo-electric crystal esophageal Doppler probe head assembly 150 configured such that the system may be driven by continuous ultrasound. More specifically, in this embodiment there are two piezo-electric crystals—one for transmission and the other for reception. Again, the ultrasound beam may be placed such that the angle of insonation is ideally 45° but may have an angle from 30° to 60°.

It should be appreciated that another aspect of the invention is to provide enhanced focusing capability of the Doppler ultrasound flow monitor by way of a wider beam angle and use of pulse wave Doppler ultrasound to restrict the depth of view and minimize confounding signals. The esophageal pulse wave Doppler probe may also be configured to measure diameter by using multiple moving receiver gates 240 to establish the boundaries of major arteries using pulse wave ultrasound Doppler technology. Once the boundaries of the artery are established, the device can compute the arterial diameter which can then be used to automatically position the flow detection receiver gate 250 around the center of the artery. The device can further use the boundary recognition and arterial diameter computation to detect movement of the probe where detection of probe movement is achieved by changes in the apparent diameter of the artery as detected by the pulse wave beam. The user may be alerted to such movement of the probe by way of an on-screen warning and request to refocus as required.

In certain embodiments, a user may be provided with a variety of modes of measurement to suit the application. It is envisaged that the monitor will allow the connection of alternate probes and sensors for flow and pressure measurement. Additionally, monitor lines measuring oxygen concentration may also be connected to the monitor. Flow based Doppler ultrasound measurements will be available either by way of esophageal placement of the ultrasound for minimally invasive measurement in the descending aorta or by way of non-invasive suprasternal placement for measurement in the ascending aorta. Pressure measurements may be obtained either invasively from an arterial line placed in either the radial, femoral, dorsalis pedis or brachial artery or by way of blood pressure in the brachial artery using an upper arm cuff or by way an infrared light optical sensor measuring pulse pressure in the patient's fingertip.

Data from both the blood flow and blood pressure measurement sensors may be analyzed to provide real-time displays of the left ventricular flow waveform. The Doppler measurement may be utilized to frequently calibrate the pressure wave so providing continuous and accurate vascular flow information during any temporary loss of Doppler ultrasound sensor measurement due to loss of beam focus or electromagnetic interference. The data may also be processed to provide an extensive range of hemodynamic parameters for clinical use.

Alternatively the device may compute Doppler measurements to frequently calculate arterial blood pressure so providing continuous and accurate vascular pressure information during any temporary loss of signal from the arterial pressure transducer.

Figure 2A:
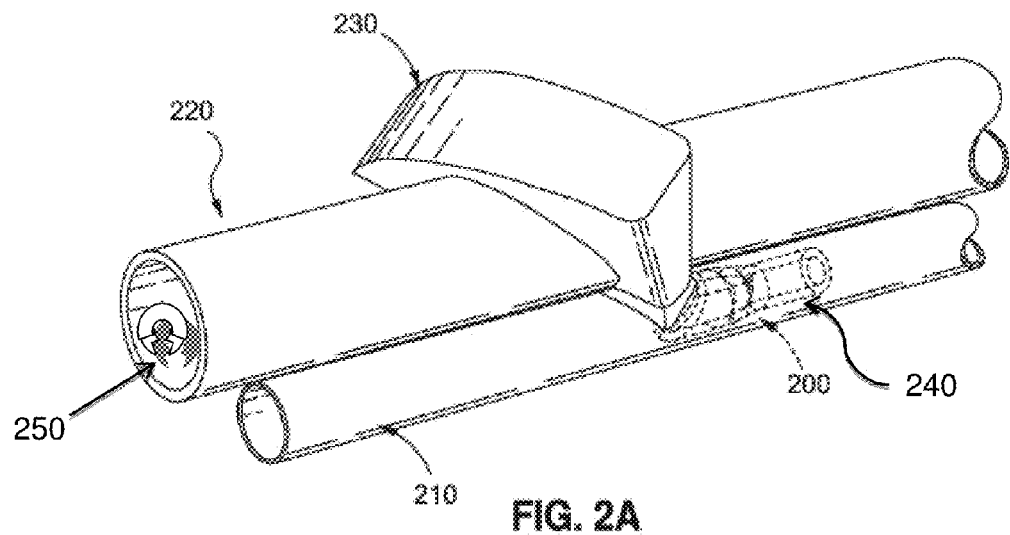
FIG. 2A is an illustration of the ultrasound beam shape produced by the high aspect ratio piezo-electric crystal with the highly divergent beam shape laterally and narrower less divergent beam longitudinally.

Referring now to FIG. 2A, depicted is one example of the orientation between a piezo-electric crystal assembly 200 (e.g., probe 100) situated within the esophagus 210, which of course is oriented adjacent to the descending aorta 220. The piezo-electric crystal (e.g., piezo-electric crystal(s) 110) may possess a high aspect ratio such that in the lateral plane the piezo-electric crystal is considerably shorter in length than in the longitudinal plane. The resulting ultrasound beam 230 resulting from such a high aspect ratio piezo-electric crystal shape is illustrated in FIG. 2A as being highly divergent in the laterally axis and less divergent in the longitudinal axis.

Figure 2B:
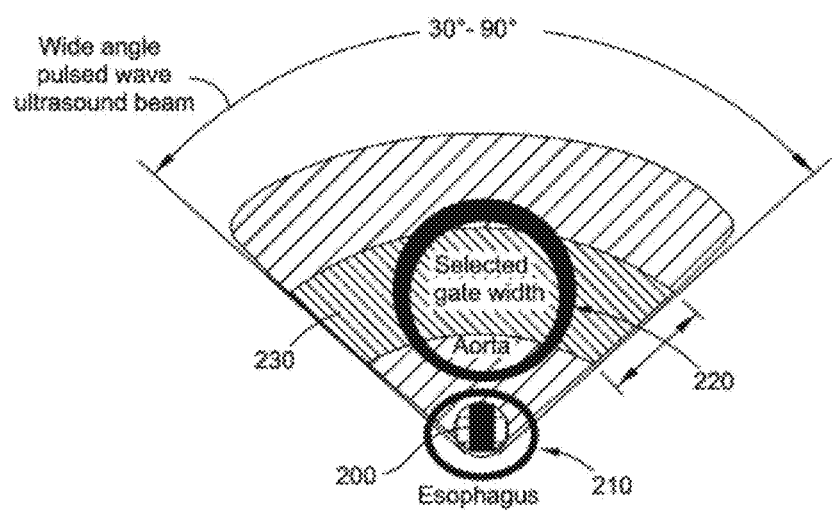
FIG. 2B is a plan view of the arrangement of FIG. 2A.

FIG. 2B depicts a plan view of the arrangement of FIG. 2A, and in particular a divergent ultrasound beam of 30° to 90° with wide focus range. The piezo-electric crystal for esophageal placement may possess a high aspect ration such that in the lateral plane the piezo-electric crystal would be shorter in length than in the longitudinal plane. A broad beam of 30° to 90° widens the useful field of view such that the wider the angle of the beam the more signal acquisition can be maintained even if the probe tip is partly rotated inadvertently due to patient or user movement. Pulse wave ultrasound provides the capability of selectively gating the target distance for measurement. The narrow focus range of the flow detection receiver gate width tends to precisely select the target blood flow within the aorta 220 and removes potentially confounding ultrasound waveforms from other vessels of the body. The selection of gating may be used to allow the detection of zones of zero blood flow conferring the ability to measure the diameter of major arteries, where the arterial diameter is used to position the probe using flow detection windows around the center of the artery and detection of probe movement by the position of the arterial wall.

Figure 3:
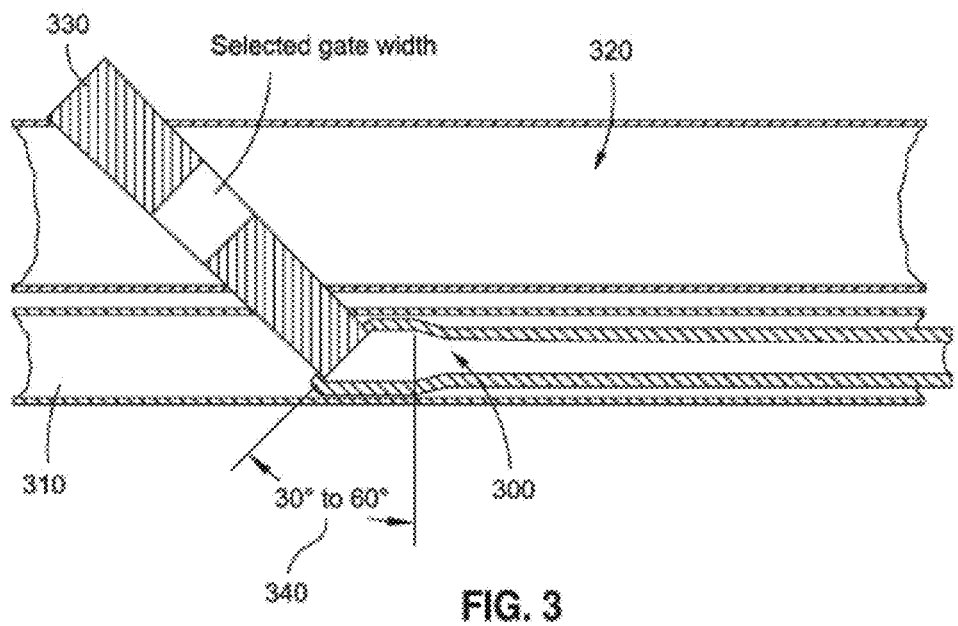
FIG. 3. is a side elevation of the arrangement of FIG. 2A showing the longitudinal ultrasound beam shape and angle of insonation.

FIG. 3 depicts still another perspective of the positioning of a piezo-electric crystal esophageal Doppler probe 300, configured in accordance with the principles of the invention, within an esophagus 310 and adjacent to the aorta 320. It should be appreciated that, in the longitudinal plane, the piezo-electric crystal of the probe 300 is typically longer in length than the lateral aspect. This crystal shape provides a less divergent ultrasound beam so maintaining more precisely the angle of insonation. Accordingly, the beam 330 may be directed such that the angle of insonation 340 is between 30° to 60°, and preferably around 45°.

Figure 4:
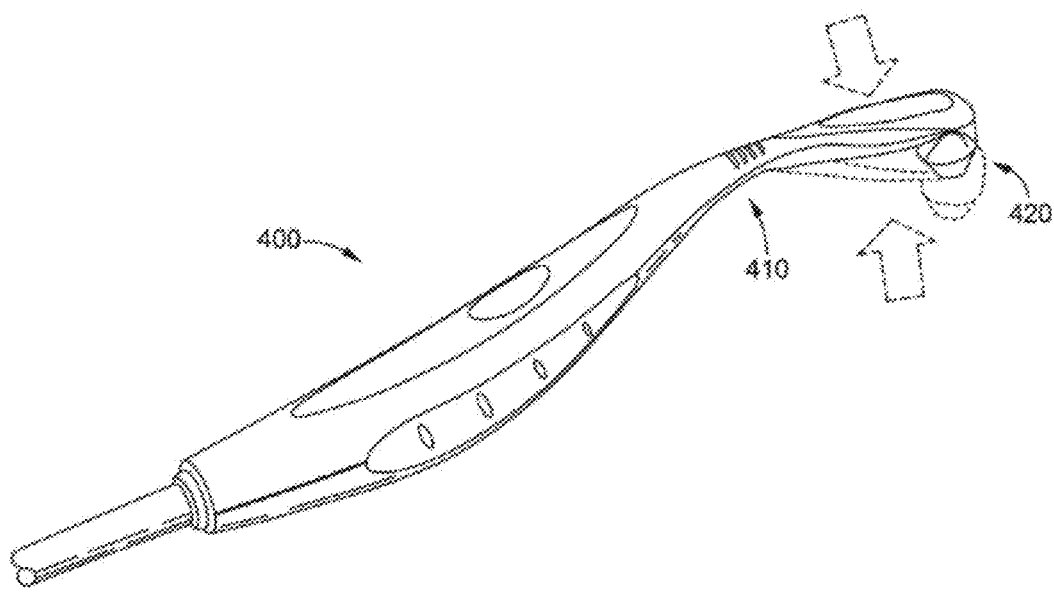
FIG. 4 is an illustration of the flexible head of the suprasternal probe handle design.

FIG. 4 depicts a pulsed wave ultrasound probe 400 for non-invasive measurement of the aortic blood flow for placement at the suprasternal notch, and configured in accordance with the principles of the invention. As shown in FIG. 4, the pulse wave suprasternal probe 400 may include an ultrasound piezo-electric crystal head assembly, such as the head assembly 100 or 150 of FIGS. 1A-1B, in a handheld probe configuration. The probe 400 may be placed in the suprasternal notch of the patient found at the superior border of the manubrium of the sternum, between the clavicular notches. The probe 400 is designed with a flexible neck 410 behind the ultrasound crystal assembly 420 such that the piezo-electric crystal head assembly can be manipulated behind the patient's sternum to achieve the optimal signal. This design may be utilized as either a single-patient-use disposable assembly to minimize cross infection risks, or as a multiple-use or reusable assembly requiring cleaning between uses.

In accordance with the principles of the invention, the monitor may utilize a wide range of measurement combinations for a variety of medical applications. By way of example, such measurement combinations may include the measurement of aortic blood flow by way of a continuous wave or pulse wave esophageal Doppler probe positioned in the patient's esophagus, as described in detail herein. The measurement combination may further include one or more of a pulse wave suprasternal probe placed externally at the suprasternal notch, an arterial line placed in either the radial, femoral, dorsalis pedis or brachial arteries, intermittent non-invasive blood pressure measurement from one of either an electronic transducer blood pressure measurement from one of either an electronic transducer blood pressure sphygmomanometer on the arm or finger cot infrared light optical pulse detector, a central venous pressure line, a continuous SvO2 monitoring line. A monitor configured in accordance with the principles of the invention may possess all or a selection of these transducer or signal input sources, depending on the chosen application.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A hemodynamic monitoring device comprising:
   one or more blood flow sensors;
   one or more blood pressure sensors in a pressure transducer system;
   an esophageal Doppler ultrasound probe configured to measure, real time, blood flow in an adjacently located artery of a human subject using ultrasound waves, wherein the probe is further configured to provide real time blood flow measurement information based on said measured blood flow;
   the pressure transducer system configured to provide a pressure sensor input and receive continuous real time blood pressure information corresponding to arterial pressure within said adjacently-located artery, wherein the real time arterial pressure is measured simultaneously with said blood flow measurement; and
   a monitor, connected to the probe, the probe configured to provide a pulse wave Doppler ultrasound with a wide beam angle to restrict the depth of view and minimize confounding signals, and the monitor configured to provide a continuous and accurate real time display of blood flow information and blood pressure information obtained from the one or more blood flow sensors and one or more blood pressure sensors, wherein the probe is further configured to measure blood vessel diameter using multiple moving receiver gates configure to establish one or more boundaries of an artery using the pulse-wave Doppler ultrasound;
   wherein the monitor is further configured to process said blood flow measurement information and blood pressure information to provide hemodynamic parameters corresponding to the human subject.

2. The hemodynamic monitoring device of claim 1, wherein said probe is configured to measure the arterial pressure simultaneously with the blood flow using said ultrasound waves.

3. The hemodynamic monitoring device of claim 1, wherein the monitor is configured to provide the hemodynamic parameters by displaying said hemodynamic parameter in real-time.

4. The hemodynamic monitoring device of claim 1, wherein the monitor is configured to provide the hemodynamic parameters by displaying said hemodynamic parameters as trended hemodynamic parameters averaged over time.

5. The hemodynamic monitoring device of claim 1, wherein the probe is configured to measure blood flow.

6. The hemodynamic monitoring device of claim 1, wherein a plurality of cardiac function parameters are derived from a combination of the blood flow measurement information and the blood pressure information.

7. The hemodynamic monitoring device of claim 1, wherein said input is configured to receive blood pressure information from at least one of an electronic pressure transducer placed in a vein, an electronic transducer blood pressure sphygmomanometer on the arm, and a finger cot infrared light optical pulse detector.

8. The hemodynamic monitoring device of claim 1, further comprising an input configured to receive signals from a mixed oxygen saturation sensor placed in a vein.

9. The hemodynamic monitoring device of claim 1, wherein the data processor is configured to derive estimated blood flow from said blood pressure information.

10. The hemodynamic monitoring device of claim 1, wherein the data processor is configured to derive estimated blood pressure from said blood flow measurement information.

11. The hemodynamic monitoring device of claim 1, wherein the probe is further configured to use the blood vessel diameter to effect positioning of a flow detection receiver gate around a center of a cross section of the artery.

12. The hemodynamic monitoring device of claim 1, wherein the device comprises a movement sensor which is configured to detect a movement of the probe based on changes in an apparent diameter of the blood vessel.

13. The hemodynamic monitoring device of claim 1, wherein the adjacently-located artery is selected from the group consisting of: a radial, brachial, dorsalis pedalis and femoral artery.

14. A method for measurement of central vascular blood flow simultaneously with arterial blood pressure comprising the acts of;
   providing one or more blood flow sensors;
   providing one or more blood pressure sensors of a pressure transducer system;

measuring in real time blood flow in a human artery using an adjacently-located esophageal Doppler ultrasound probe;

providing, using said ultrasound probe, real time blood flow measurement information based on said measured blood flow;

measuring, in real time via the pressure transducer system, arterial pressure within said human artery simultaneously with said measuring blood flow measurement;

providing, via the pressure transducer system, a pressure sensor input and real time blood pressure information corresponding to said measured arterial pressure within said adjacently-located artery; and providing using the probe and a monitor connected to the probe, a pulse wave Doppler ultrasound with a wide beam angle to restrict the depth of view and minimize confounding signals and a continuous and accurate real time display of blood flow information and blood pressure information obtained from the one or more blood flow sensors and one or more blood pressure sensors;

measuring blood vessel diameter using multiple moving receiver gates configured to establish one or more boundaries of an artery using the pulse-wave Doppler ultrasound; and providing, via the probe further configured to process blood flow and blood measurement information, hemodynamic parameters corresponding to the human subject based on a combination of said blood flow measurement information and blood pressure information.

15. The method of claim 14, wherein measuring the arterial pressure simultaneously with measuring the blood flow comprises measuring the arterial pressure using said adjacently-located ultrasound probe.

16. The method of claim 14, wherein providing hemodynamic parameters further comprises displaying, via the monitor, said hemodynamic parameters in real-time.

17. The method of claim 14, wherein providing hemodynamic parameters further comprises displaying, via the monitor, said hemodynamic parameters as trended hemodynamic parameters averaged over time.

18. The method of claim 14, wherein measuring blood flow in the human artery comprises measuring blood flow in the human artery provided by the adjacently-located ultrasound probe.

19. The method of claim 14, further comprising deriving, via the probe, a plurality of cardiac function parameters from a combination of the blood flow measurement information and the blood pressure information.

20. The method of claim 14, wherein providing blood pressure information comprises providing blood pressure information using at least one of an electronic pressure transducer placed in a vein, an electronic transducer blood pressure sphygmomanometer on the arm, and a finger cot infrared light optical pulse detector.

21. The method of claim 14, further comprising receiving, via the pressure transducer system, signals from a mixed oxygen saturation sensor placed in a vein.

22. The method of claim 14, further comprising deriving, via the probe, an estimated blood flow from said blood pressure information.

23. The method of claim 14, further comprising deriving, via the probe, estimated blood pressure from said blood flow measurement information.

24. The method of claim 14, further comprising positioning, via the probe, a flow detection receiver gate around a center of a cross section of the artery based on said blood vessel diameter.

25. The method of claim 14, further comprising detecting, via a movement sensor, a movement of the probe based on changes in an apparent diameter of the blood vessel.

26. The method of claim 14, wherein the human artery is selected from the group consisting of: a radial, brachial, dorsalis pedalis and femoral artery.

* * * * *